United States Patent
Kostova et al.

(10) Patent No.: US 8,420,879 B2
(45) Date of Patent: Apr. 16, 2013

(54) PROCESS FOR WORKUP OF A STREAM COMPRISING BUTENE AND/OR BUTADIENE

(75) Inventors: Albena Kostova, Mannheim (DE); Regina Benfer, Altrip (DE); Jochen Götz, Speyer (DE); Alireza Rezai, Mannheim (DE); Aristides Morillo, Katy, TX (US); Gerhard Olbert, Dossenheim (DE); Peter Pfab, Shaker Heights, OH (US); Grigorios Kolios, Neustadt (DE); Markus Weber, Limburgerhof (DE); Alexander Weck, Freinsheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/411,080

(22) Filed: Mar. 2, 2012

(65) Prior Publication Data

US 2012/0226087 A1    Sep. 6, 2012

Related U.S. Application Data

(60) Provisional application No. 61/448,672, filed on Mar. 3, 2011.

(51) Int. Cl.
*C07C 7/08* (2006.01)

(52) U.S. Cl.
USPC ............ 585/809; 585/810; 585/833; 585/860

(58) Field of Classification Search .......................... None
See application file for complete search history.

(56) References Cited

U.S. PATENT DOCUMENTS

| | | |
|---|---|---|
| 2007/0055088 A1 | 3/2007 | Schindler et al. |
| 2007/0244349 A1 | 10/2007 | Crone et al. |
| 2008/0097133 A1 | 4/2008 | Crone et al. |
| 2008/0119680 A1 | 5/2008 | Crone et al. |
| 2008/0183024 A1 * | 7/2008 | Klanner et al. .............. 585/633 |

FOREIGN PATENT DOCUMENTS

| | | |
|---|---|---|
| DE | 102004059356 A1 | 6/2006 |
| DE | 102004061514 A1 | 7/2006 |
| EP | 1682468 A1 | 7/2006 |
| SU | 1159915 A1 | 6/1985 |
| WO | WO-2006050969 A1 | 5/2006 |

OTHER PUBLICATIONS

U.S. Appl. No. 12/950,646, filed Nov. 19, 2010, Steiner et al.
U.S. Appl. No. 12/957,618, filed Dec. 1, 2010, Kolios et al.
U.S. Appl. No. 61/425,280.
U.S. Appl. No. 61/491,911.

* cited by examiner

*Primary Examiner* — Tam M Nguyen
(74) *Attorney, Agent, or Firm* — Novak Druce Connolly Bove + Quigg LLP

(57) ABSTRACT

The invention relates to a process for workup of a stream (1) comprising butene and/or butadiene, butane, hydrogen and/or nitrogen and carbon dioxide, comprising:

(a) absorption of stream (1) with a mixture (5) comprising 80 to 97% by weight of N-methylpyrrolidone and 3 to 20% by weight of water to obtain a stream (9) comprising N-methylpyrrolidone, water, butene and/or butadiene, butane, and optionally carbon dioxide, and a stream (7) comprising hydrogen and/or nitrogen and butane, (b) extractive distillation of stream (9) with a stream (13) comprising 80 to 97% by weight of N-methylpyrrolidone and 3 to 20% by weight of water to separate the stream (9) into a stream (17) comprising N-methylpyrrolidone, water, butene and/or butadiene, and a stream (15) comprising essentially butane, and optionally carbon dioxide, (c) distillation of stream (17) into a stream (23) comprising essentially N-methylpyrrolidone and water, and a stream (21) comprising butene and/or butadiene.

9 Claims, 1 Drawing Sheet

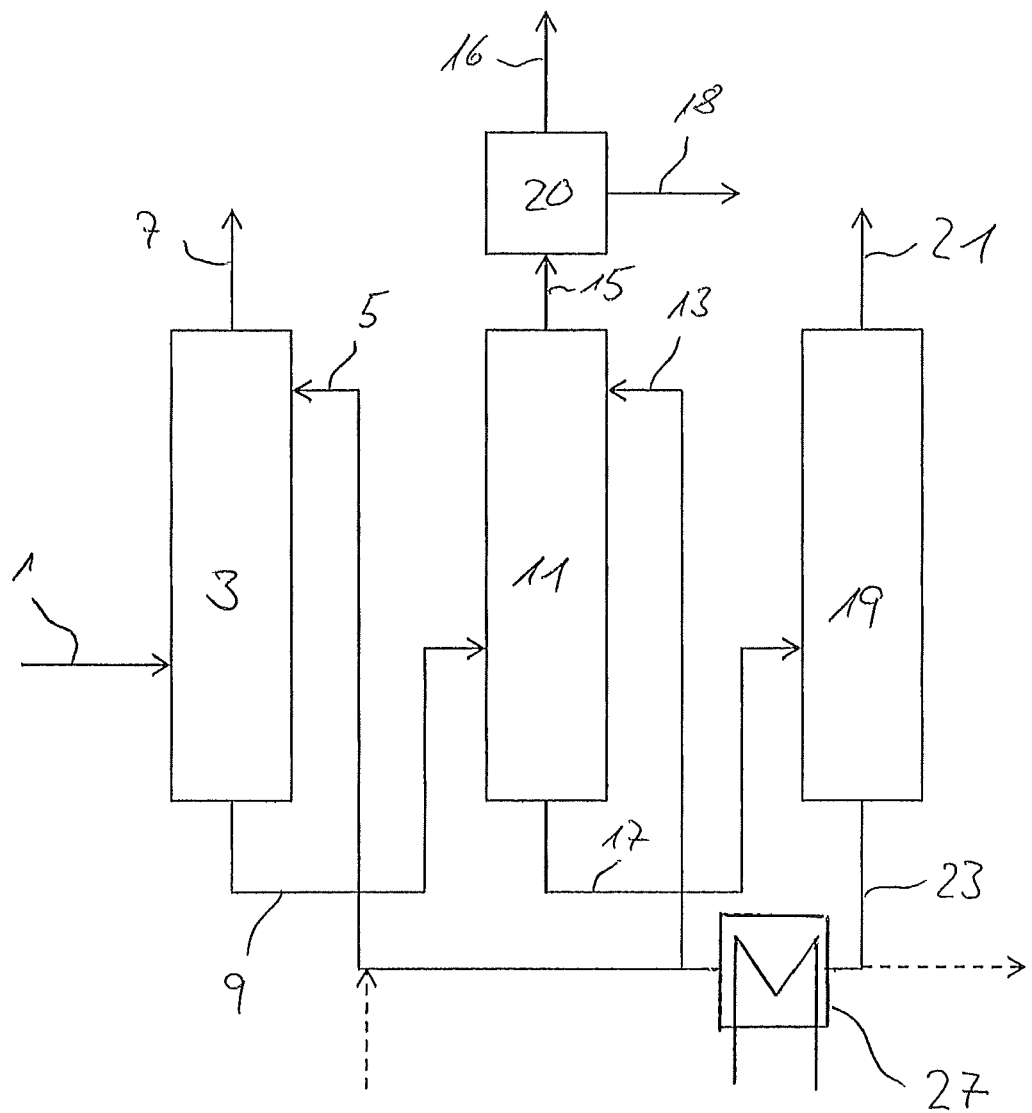

PROCESS FOR WORKUP OF A STREAM COMPRISING BUTENE AND/OR BUTADIENE

CROSS-REFERENCE TO RELATED APPLICATIONS

This application claims the benefit of U.S. Provisional Application 61/448,672, filed Mar. 3, 2011, which is incorporated by reference.

BACKGROUND OF THE INVENTION

The invention relates to a process for workup of a stream comprising butene and/or butadiene, butane, hydrogen and/or nitrogen, with or without carbon dioxide.

Butenes and butadiene can be prepared, for example by thermal cleavage (steam-cracking) of saturated hydrocarbons, typically proceeding from naphtha as a raw material. The steamcracking of naphtha gives a hydrocarbon mixture of methane, ethane, ethene, acetylene, propane, propene, propyne, allene, methylallene, and $C_5$ and higher hydrocarbons.

A disadvantage of this process for producing butenes and butadiene is that relatively large amounts of unwanted coproducts are inevitably obtained. Alternatively, the butenes can be prepared from butane and butadiene from n-butene, by dehydrogenation.

DE-A 10 2004 059 356 discloses, for example, preparing butadiene by using n-butane as a feedstock. To prepare the butadiene, the n-butane is dehydrogenated in a dehydrogenation zone by nonoxidative catalytic dehydrogenation to give a stream comprising n-butane, 1-butene, 2-butene, butadiene, and hydrogen, with or without carbon dioxide and with or without water vapor. In a second dehydrogenation zone, the 1-butene and 2-butene are dehydrogenated further to butadiene. The stream obtained in the dehydrogenation is subsequently compressed and cooled in order to condense out water. A product stream comprising essentially butadiene is removed by extractive distillation from the residual stream comprising n-butane, butadiene, hydrogen, carbon dioxide and water vapor.

A corresponding process for preparing butadiene from n-butane is additionally also described in DE-A 10 2004 061 514.

A disadvantage of the process described here is that a different solvent than in the extractive distillation is used for the removal of an $H_2$-rich stream in the absorption, and thus a desorption stage for the $H_2$-rich gas is also needed. In addition there is no separation of $CO_2$ and $H_2$.

A further process for workup of a stream comprising butenes is also known from SU-A 1159915. In this process, the stream comprising butenes is subjected first to an absorption and then to an extractive distillation. The solvent used for the absorption and the extractive distillation is acetonitrile. A disadvantage in the case of the use of acetonitrile is that it does not dissolve any carbon dioxide. The use of acetonitrile therefore leads to the effect that the proportion of carbon dioxide in the gas increases since the carbon dioxide is recycled into the butane dehydrogenation together with the hydrogen and is not washed out in the absorption.

WO-A 2006/050969 describes a process for preparing butadiene from n-butane, in which the butadiene-comprising stream from the dehydrogenation is first cooled in order to condense out water. In a further compression stage and cooling, a condensate stream comprising n-butane, butadiene and water is obtained. n-Butane and butadiene are removed from the stream comprising water, n-butane and butadiene, and then separated into a product stream consisting essentially of butadiene and a recycle stream comprising n-butane.

A disadvantage here is that the $C_4$ components are removed from the inert gases by a multistage compression and subsequent condensation. This process stage features a high energy requirement for the compression up to approx. 30 bar. The $C_4$ condensation is effected at a temperature of 10° C., and thus a cooling unit is additionally required.

A process for preparing 1-butene is described, for example, in EP-B 1 682 468. In the process described here, a $C_4$ stream is removed in a two-stage process by absorption and a subsequent desorption of inerts. A disadvantage of the process is that the absorption solvent (tetradecane) is different than the solvent used in the extractive distillation (NMP). Moreover, there is the risk of mixing of the two solvents, which results in a reduced selectivity of the absorption and extractive distillation stages. A further disadvantage here is that the absorbent is selective only for $C_4$ and hence there is no removal of $H_2$ and $CO_2$. The use of different solvents in the absorption step entails a desorption of the $C_4$ component with steam before it is passed on into the NMP extractive distillation column.

It is an object of the present invention to provide a process for workup of a stream comprising butene and/or butadiene, which can be implemented with less complexity and lower costs.

BRIEF SUMMARY OF THE INVENTION

The object is achieved by a process for workup of a stream comprising butene and/or butadiene, butane, hydrogen and/or nitrogen, with or without carbon dioxide, comprising the following steps:

(a) absorption of the stream comprising butene and/or butadiene, butane, hydrogen and/or nitrogen, with or without carbon dioxide, with a mixture comprising 80 to 97% by weight of N-methylpyrrolidone and 3 to 20% by weight of water to obtain a stream comprising N-methylpyrrolidone, water, butene and/or butadiene, and butane, with or without carbon dioxide, and a stream comprising hydrogen and/or nitrogen and butane, (b) extractive distillation of the stream comprising N-methylpyrrolidone, water, butene and/or butadiene, and butane, with or without carbon dioxide, with a stream comprising 80 to 97% by weight of N-methylpyrrolidone and 3 to 20% by weight of water to separate the stream comprising N-methylpyrrolidone, water, butene and/or butadiene, and butane, with or without carbon dioxide, into a stream comprising N-methylpyrrolidone, water, butene and/or butadiene, and a stream comprising essentially butane, with or without carbon dioxide, (c) distillation of the stream comprising N-methylpyrrolidone, water, butene and/or butadiene into a stream comprising essentially N-methylpyrrolidone and water, and a stream comprising butene and/or butadiene.

According to the invention, a mixture of 80 to 97% by weight of N-methylpyrrolidone and 3 to 20% by weight of water, preferably a mixture of 90 to 93% by weight of N-methylpyrrolidone and 7 to 10% by weight of water and especially a mixture of 91 to 92% by weight of N-methylpyrrolidone and 8 to 9% by weight of water, for example a mixture of 91.7% by weight of N-methylpyrrolidone and 8.3% by weight of water, is used both as the solvent for the absorption in step (a) and as the extractant for the extraction in step (b).

BRIEF DESCRIPTION OF THE FIGURES

FIG. 1 shows a working example of the invention.

DETAILED DESCRIPTION OF THE INVENTION

The process according to the invention is notable for particularly effective removal of the butenes and/or of the butadiene. Thus, losses resulting from incomplete condensation of the butenes and/or of the butadiene are minimized. The process according to the invention proceeds at lower pressures than a $C_4$ condensation and does not require low temperatures. The process is thus more energetically efficient than the processes known from the prior art. In contrast to absorption/desorption processes followed by an extractive distillation, the same solvent is used in the process according to the invention, with a reduction in the number of columns needed. In addition, it is also impossible for different solvents to mix.

The use of a mixture of N-methylpyrrolidone and water as a solvent for the absorption and as an extractant in the extractive distillation has the advantage that the boiling point is lower than the boiling point in the case of use of pure N-methylpyrrolidone. A further advantage is that increasing the water content in the mixture of water and N-methylpyrrolidone used as the solvent can enhance the selectivity. However this leads as expected to a reduction in the capacity. A further advantage is the selectivity of the N-methylpyrrolidone for carbon dioxide. This enables, in addition to the removal of the hydrocarbons, a removal of the carbon dioxide from the hydrogen.

In the context of the present invention, butene is always understood to mean 1-butene, 2-butene (cis and trans) and isobutene. In this context, the different butenes may each occur individually or in any mixtures with one another.

The stream comprising butene and/or butadiene, butane, hydrogen and/or nitrogen, with or without carbon dioxide, may originate, for example, from a butane dehydrogenation and/or a butene dehydrogenation.

A butene-rich stream can arise, for example, as a product stream in a butane dehydrogenation and comprises generally 20 to 70% by volume of butane (n-butane, isobutane), 0 to 40% by volume of isobutene, 1 to 15% by volume of 1-butene, 1 to 25% by volume of 2-butene (cis/trans-butene), 0.1 to 15% by volume of butadiene, 1 to 70% by volume of water vapor, 0.1 to 40% by volume of hydrogen, 0 to 10% by volume of nitrogen, 0 to 10% by volume of low-boiling hydrocarbons (ethane, ethene, methane, propane, propene) and 0 to 5% by volume of carbon oxides.

The starting material supplied to the butane dehydrogenation is a use gas stream which comprises generally at least 60% by weight of butane, preferably at least 90% by weight of butane. In addition, it may also comprise $C_1$-$C_6$ hydrocarbons as secondary constituents. The butane dehydrogenation can be conducted as a catalytic non-oxidative or oxidative dehydrogenation. The butane supplied can be added as n-butane, as isobutane or as a mixture of n-butane and isobutane. Preference is given to adding n-butane.

In a nonoxidative catalytic dehydrogenation, the butane-comprising use gas stream is fed into a dehydrogenation zone and subjected to the nonoxidative catalytic dehydrogenation. This involves partly dehydrogenating n-butane in a dehydrogenation reactor over a dehydrogenation-active catalyst to give 1-butene and 2-butene, also forming butadiene. In addition, hydrogen and small amounts of methane, ethane, ethene, propane and propene are obtained. According to the mode of operation of the dehydrogenation, it is also possible for carbon oxides (carbon monoxide and carbon dioxide), water and nitrogen to be present in the product gas mixture of the nonoxidative catalytic n-butane dehydrogenation. In addition, unconverted butane is present in the product gas mixture of the nonoxidative catalytic dehydrogenation.

The nonoxidative n-butane dehydrogenation can in principle be performed in all reactor types and modes of operation known from the prior art. A comparatively detailed description of suitable dehydrogenation processes is also present in "Catalytica® Studies Division, Oxidative Dehydrogenation and Alternative Dehydrogenation Processes" (Study No. 412 OD, 1993, 430 Ferguson Drive, Mountain View, Calif., 94043-5272, USA).

The nonoxidative catalytic butane dehydrogenation can be performed with or without oxygenous gas as a cofeed. It is preferably performed as an autothermal non-oxidative dehydrogenation with supply of oxygen as a co-feed. In the autothermal mode of operation, the heat required is produced directly in the reactor system by combustion of hydrogen and/or hydrocarbons in the presence of oxygen. Optionally, it is additionally possible to add a hydrogen-comprising co-feed. In at least one reaction zone, oxygen is additionally added to the reaction gas mixture of the n-butane dehydrogenation, and the hydrogen and/or hydrocarbon present in the reaction gas mixture is at least partly combusted, which generates at least a portion of the heat of dehydrogenation required in the at least one reaction zone directly in the reaction gas mixture. Oxygen can be fed in as an oxygen/steam mixture or as an air/steam mixture. By virtue of the use of an oxygen/steam mixture, only small amounts of inert gases (nitrogen) are introduced into the overall process.

In general, the amount of the oxygenous gas added to the reaction gas mixture is selected such that the combustion of hydrogen present in the reaction gas mixture and of any hydrocarbons present in the reaction gas mixture and/or of carbon present in the form of coke generates the amount of heat required for the dehydrogenation of the butane. In general, the total amount of oxygen supplied, based on the total amount of butane, is 0.001 to 0.5 mol/mol, preferably 0.005 to 0.2 mol/mol, more preferably 0.05 to 0.2 mol/mol.

The hydrogen combusted to generate heat is hydrogen formed in the catalytic butane dehydrogenation and optionally hydrogen added additionally as a hydrogenous gas to the reaction gas mixture. Preferably, a sufficient amount of hydrogen should be present that the molar $H_2/O_2$ ratio in the reaction gas mixture immediately after the feeding of oxygen is 1 to 10, preferably 2 to 5 mol/mol. In the case of multistage reactors, this applies to each intermediate feeding of oxygenous, and optionally hydrogenous, gas.

The hydrogen is combusted catalytically. The dehydrogenation catalyst used generally also catalyzes the combustion of the hydrocarbons and of hydrogen with oxygen, and so in principle no specific oxidation catalyst is required. Suitable catalysts are described, for example, in DE-A 10 2004 061 514.

In one embodiment of the process according to the invention, there is intermediate feeding of oxygenous gas and hydrogenous gas upstream of each stage of a staged reactor. In a further embodiment of the process according to the invention, oxygenous gas and hydrogenous gas are fed in upstream of every stage except the first stage. In one embodiment, beyond each feed point, a layer of a specific oxidation catalyst is present, followed by a layer of the dehydrogenation catalyst. In a further embodiment, no specific oxidation catalyst is present. The dehydrogenation temperature is generally 400 to 1100° C., the pressure in the last catalyst bed of the staged reactor generally 0.2 to 5 bar, preferably 1 to 3 bar. The space velocity (GHSV) is generally 500 to 2000 $h^{-1}$, and in high-load mode even up to 100 000 $h^{-1}$, preferably 4000 to 16 000 $h^{-1}$.

The butane dehydrogenation is preferably performed in the presence of water vapor. The water vapor added serves as a heat carrier and promotes the gasification of organic deposits on the catalysts, which counteracts the coking of the catalysts and increases the service life of the catalysts. This converts the organic deposits to carbon monoxide, carbon dioxide, and possibly water.

It is a feature of the nonoxidative operating mode compared to an oxidative operating mode that no free hydrogen is formed in significant amounts in the oxidative dehydrogenation.

A butadiene-rich stream can be obtained, for example, in a butene dehydrogenation. In general, the butadiene-rich stream obtained in the butene dehydrogenation comprises 10 to 40% by volume of butadiene, 15 to 79.9% by volume of n-butane, 0 to 10% by volume of 2-butene, 0 to 2% by volume of 1-butene, 10 to 70% by volume of water vapor, 0 to 10% by volume of low-boiling hydrocarbons (methane, ethane, ethene, propane and propene), 0.1 to 15% by volume of hydrogen, 0 to 10% by volume of nitrogen, 0 to 15% by volume of carbon dioxide and 0 to 7% by volume of oxygenates. Oxygenates may be, for example, furan, acetic acid, maleic anhydride, maleic acid, propionic acid, acetaldehyde, acrolein, formaldehyde, formic acid and butyraldehyde. In addition, traces of acetylene, propyne and 1,2-butadiene may be present.

The butene dehydrogenation can be operated as an individual process or in combination with a butane dehydrogenation. The butene dehydrogenation can be operated nonoxidatively or oxidatively (with an $O_2$-rich gas as an oxidizing agent).

Preference is given to oxidative butene dehydrogenation. The oxidative dehydrogenation can in principle be performed in all reactor types and operating modes known from the prior art, for example, in a fluidized bed, in a staged oven, in a fixed bed tubular or tube bundle reactor, or in a plate heat exchanger reactor. Performance of the oxidative dehydrogenation requires a gas mixture which has a molar oxygen:n-butenes ratio of at least 0.5. Preference is given to working at an oxygen:n-butenes ratio of 0.55 to 50. To adjust this value, the product gas mixture originating from the nonoxidative catalytic dehydrogenation is generally mixed with pure oxygen or an oxygenous gas, directly or after a workup in which butenes are concentrated and hydrogen is removed. In one embodiment the oxygenous gas comprises, as in the case of the first (autothermal) dehydrogenation stage, predominantly oxygen, at least 75% by volume, preferably at least 90% by volume, in order to minimize the inert gas content in the product gas stream of the oxydehydrogenation. In this case, oxygen of technical grade purity is preferred. The resulting oxygenous gas mixture is then supplied to the oxydehydrogenation. A preferable alternative to an oxygenous gas comprising at least 75% by volume of oxygen is to use air or lean air with a proportion of less than 23% by volume as the oxygenous gas.

The oxydehydrogenation is performed generally at a temperature of 220 to 490° C. and preferably of 250 to 450° C. A reactor inlet pressure sufficient to overcome the flow resistances present in the plant and the downstream workup is selected. This reactor inlet pressure is generally 0.005 to 1 MPa gauge, preferably 0.01 to 0.5 MPa gauge. Naturally, the gas pressure employed in the inlet region of the reactor declines substantially over the overall bed of catalyst.

The product gas stream leaving the oxidative dehydrogenation comprises, as well as butadiene and unconverted n-butane, also hydrogen, carbon dioxide and water vapor. As secondary constituents it may also comprise oxygen, nitrogen, methane, ethane, ethene, propane and propene, and oxygenous hydrocarbons, called oxygenates. In general, it comprises virtually no 1-butene any longer and only small proportions of 2-butene.

In a preferred embodiment, water is removed from the product stream after the dehydrogenation. The water is preferably removed in a quench.

The stream which comprises butadiene and/or butene, butane, hydrogen and/or nitrogen, with or without carbon dioxide and which may originate from an oxydehydrogenation or nonoxidative dehydrogenation after partial condensation of water vapor, is supplied as a starting stream to step (a) of the workup.

The absorption in step (a) can be performed in any desired suitable absorption column known to those skilled in the art. Preference is given to performing the absorption in countercurrent. For this purpose, the stream comprising butene and/or butadiene, butane, hydrogen and/or nitrogen, with or without carbon dioxide, is supplied to the absorption column in the lower region. In the upper region of the absorption column, the stream comprising N-methylpyrrolidone and water is introduced.

At the top of the absorption column, a hydrogen-rich and/or nitrogen-rich stream is withdrawn, which may also comprise residues of $C_4$ hydrocarbons and possibly carbon oxygenates. In addition, this stream may comprise inerts (for example, nitrogen) and low boilers (ethane, ethene, propane, propene, methane). The stream comprising N-methylpyrrolidone and water cools the supplied stream comprising butene and/or butadiene, butane, hydrogen and/or nitrogen, with or without carbon dioxide, and at the same time preferentially absorbs the $C_4$ components and some $CO_2$. In some cases, small amounts of $H_2$, inerts ($N_2$) and low boilers are also absorbed. This stream is drawn off at the bottom of the absorption column.

The absorption in step (a) is performed generally at a bottom temperature in the range from 30 to 160° C., a top temperature in the range from 5 to 60° C., and a pressure in the range from 2 to 20 bar. Preference is given to performing the absorption at a bottom temperature in the range from 30 to 100° C., a top temperature in the range from 25 to 50° C. and a pressure in the range from 8 to 15 bar.

The absorption column is preferably a column with random packing or a column with structured packing. However, any other column is also conceivable, for example a tray column. A column suitable for the absorption preferably has 2 to 40 theoretical plates, preferably 5 to 25 theoretical plates.

The temperature of the stream which comprises N-methylpyrrolidone and water and is supplied to the absorption column is preferably 10 to 70° C., more preferably 20 to 40° C. The temperature of the stream comprising butene and/or butadiene, butane, hydrogen and/or nitrogen, with or without carbon dioxide, is preferably in the range between 0 and 400° C., especially in the range between 40 and 200° C.

The ratio of N-methylpyrrolidone used to stream comprising butene and/or butadiene, butane, hydrogen and/or nitrogen, with or without carbon dioxide, is preferably in the range from 2 to 30, more preferably in the range from 4 to 30 and especially in the range from 4 to 15, based in each case on the masses of the streams used.

The stream which comprises N-methylpyrrolidone, water, butene and/or butadiene, butane and carbon dioxide, and is obtained in the absorption, comprises generally 20 to 90 mol % of N-methylpyrrolidone, 0 to 50 mol % of water, 0 to 20 mol % of butadiene, 0 to 20 mol % of 1-butene, 0 to 20 mol % of 2-butene, 0 to 50 mol % of butane and 0 to 20 mol % of carbon dioxide.

The stream which comprises N-methylpyrrolidone, water, butene and/or butadiene, butane and carbon dioxide, and is obtained in the absorption, is then supplied to an extractive distillation in step (b).

The extractive distillation can be performed, for example, as described in Erdöl and Kohle-Erdgas-Petrochemie volume 34 (8), pages 343 to 346 or Ullmanns Enzyklopädie der technischen Chemie, volume 9, 4th edition 1975, pages 1 to 18.

The extractive distillation is conducted preferably at a bottom temperature in the range from 100 to 250° C., especially at a temperature in the range from 110 to 210° C., a top temperature in the range from 10 to 100° C., especially in the range from 20 to 70° C. and a pressure in the range from 1 to 15 bar, especially in the range from 3 to 8 bar. The extractive distillation column preferably has 5 to 70 theoretical plates.

In the extractive distillation, the stream comprising butene and/or butadiene, butane, N-methylpyrrolidone, water and carbon dioxide is contacted with a stream comprising N-methylpyrrolidone and water in an extractive distillation zone. The extractive distillation zone is generally configured in the form of a column which has trays, random packings or structured packings as internals. The extractive distillation has generally 10 to 70 theoretical plates, in order that a sufficiently good separating effect is achieved. The extraction column preferably has a rescrubbing zone in the top of the column. This rescrubbing zone serves for recovery of the N-methylpyrrolidone present in the gas phase by means of a liquid hydrocarbon return stream, for which the top fraction is condensed beforehand. Typical temperatures at the top of the column are between 30 and 60° C.

The top product stream of the extractive distillation column comprises butane and carbon dioxide and is drawn off in gaseous form. In addition to butane and carbon dioxide, it is also possible for butenes, hydrogen and/or nitrogen and other low boilers to be present in the top product stream. In a preferred embodiment, the top product stream is condensed in order to remove $CO_2$ and any hydrogen and/or nitrogen and low boilers present from butane. The liquid butane stream can, for example, be recycled into the dehydrogenation zone in the case of operation with a dehydrogenation.

At the bottom of the extractive distillation column, a stream comprising N-methylpyrrolidone, water, butene and/or butadiene and butane is obtained. The stream comprising N-methylpyrrolidone, water, butadiene and/or butene, with or without butane, which is obtained at the bottom of the extractive distillation column, is fed to a distillation column (c) in which butadiene and/or butene and optionally butane are obtained via the top. At the bottom of the distillation column, a stream comprising N-methylpyrrolidone and water is obtained, the composition of the stream comprising N-methylpyrrolidone and water corresponding to the composition as added to the absorption and the extraction. The stream comprising N-methylpyrrolidone and water is divided and passed back into the absorption and the extractive distillation. The ratio of the mixture of water and N-methylpyrrolidone which is supplied to the absorption to the mixture of water and N-methylpyrrolidone which is supplied to the extractive distillation is preferably in the range from 0.2 to 20, especially in the range from 0.3 to 15.

The distillation (c) is preferably performed at a bottom temperature in the range from 100 to 300° C., especially in the range from 150 to 200° C. and a top temperature in the range from 0 to 70° C., especially in the range from 10 to 50° C. The pressure in the distillation column 19 is preferably in the range from 1 to 10 bara. The distillation column 19 has preferably 2 to 30, especially 5 to 20, theoretical plates.

Alternatively to the withdrawal of the stream comprising butene and/or butadiene, with or without butane, from the distillation stage via the top, it is alternatively also possible to withdraw a butadiene-rich stream as a side draw. In this case, it is possible to deplete the top stream of butadiene.

A working example of the invention is shown in the figure and is explained in detail in the description which follows.

A stream 1 comprising butene and/or butadiene, butane, hydrogen and/or nitrogen, with or without carbon dioxide, is supplied to an absorption column 3. The addition is effected in the lower region of the absorption column 3. Via an upper feed 5, a stream comprising N-methylpyrrolidone and water is added to the absorption column 3, such that the stream comprising N-methylpyrrolidone and water, and the stream comprising butene and/or butadiene, butane, hydrogen and/or nitrogen, with or without carbon dioxide, are conducted in countercurrent in the absorption column.

The absorption column 3 is operated at a bottom temperature in the range between 30 and 160° C., preferably in the range between 30 and 100° C., a top temperature in the range from 5 to 60° C., preferably in the range from 25 to 50° C. and at a pressure in the range from 2 to 20 bar, preferably in the range from 8 to 15 bar.

At the top of the absorption column 3 a top stream 7 comprising hydrogen and/or nitrogen, residues of $C_4$ hydrocarbons and low boilers is withdrawn. In one embodiment, a portion of the top stream 7 is recycled into a butane dehydrogenation from which the supplied stream comprising butene and/or butadiene, butane, hydrogen and/or nitrogen, with or without carbon dioxide, may originate.

At the bottom of the absorption column 3, a bottom stream 9 comprising butene and/or butadiene, butane, N-methylpyrrolidone and water, with or without carbon dioxide, is drawn off.

The bottom stream 9 is added to extractive distillation column 11 in the lower region. In the upper region of the extractive distillation column 11, a stream 13 comprising N-methylpyrrolidone and water is introduced, which has the same composition as the stream comprising N-methylpyrrolidone and water supplied to the absorption. The stream 13 comprising N-methylpyrrolidone and water, and the stream 9 comprising butene and/or butadiene, butane, N-methylpyrrolidone, water, with or without carbon dioxide, are likewise conducted in countercurrent.

From the extractive distillation column 11, a stream 15 comprising butane and carbon dioxide is drawn off via the top. The stream 15 is condensed in a condenser 20. This gives rise to a liquid butane-rich stream 16 and a vaporous $CO_2$-rich stream 18. The butane-rich stream 16 can likewise be recycled into the butane dehydrogenation.

At the bottom of the extractive distillation column 11 a bottom stream 17 comprising N-methylpyrrolidone, water, butene and/or butadiene is withdrawn.

The bottom stream 17 is supplied to a distillation column 19 in which it is separated into a stream 21 which comprises butene and/or butadiene and is withdrawn at the top of the distillation column 19, and a stream 23 which comprises N-methylpyrrolidone and water and is withdrawn at the bottom of the distillation column 19.

According to the invention, for the absorption and for the extractive distillation, the solvent used is a stream comprising 80 to 97% by weight of N-methylpyrrolidone and 3 to 20% by weight of water.

The bottom stream 23 which is withdrawn from the distillation column 19 and comprises the N-methylpyrrolidone and the water is cooled in a heat exchanger 27, separated and recycled into the absorption column 3 or the extractive distillation column 11.

The extractive distillation is preferably conducted at a bottom temperature in the range from 90 to 250° C., especially at a temperature in the range from 90 to 210° C., a top temperature in the range from 10 to 100° C., especially in the range from 20 to 70° C. and a pressure in the range from 1 to 15 bar, especially in the range from 3 to 8 bar. The extractive distillation column preferably has 5 to 70 theoretical plates.

The distillation in the distillation column 19 is preferably performed at a bottom temperature in the range from 100 to 300° C., especially in the range from 150 to 200° C. and a top temperature in the range from 0 to 70° C., especially in the range from 10 to 50° C. The pressure in the distillation column 19 is preferably in the range from 1 to 10 bara. The distillation column 19 has preferably 2 to 30, especially 5 to 20, theoretical plates.

EXAMPLES

Example 1

A stream 1 comprising hydrogen, n-butane, butenes and butadiene is added to an absorption column 3 in the lower region. In the upper region of the absorption column, N-methylpyrrolidone containing 8.3% by weight of water is introduced as a solvent. At the top of the column, a top stream 7 comprising hydrogen and butane is withdrawn. At the bottom, a bottom stream 9 comprising N-methylpyrrolidone, water, butanes, butenes, butadiene and carbon dioxide is obtained. The absorption column used is a bubble-cap tray column with 70 bubble-cap trays having a diameter of 50 mm. The hydrocarbon feed stream is added above the tenth bubble-cap tray, and the solvent with a mass flow rate of 16 kg/h above the 60th bubble-cap tray. The inlet temperature of the solvent is 35° C. The absorption is performed at a top temperature of 33° C., a bottom temperature of 51° C. and a pressure of 10 bara. The mass ratio of solvent to added stream 1 comprising hydrogen, n-butane, butenes and butadiene is 9.9.

The bottom stream 9 withdrawn from the absorption column is added to an extractive distillation column 11 as a feed in the lower region. In the upper region, a solvent comprising N-methylpyrrolidone and 8.3% by weight of water is added to the extractive distillation column. At the top of the extractive distillation column, a top product stream 15 is obtained which comprises butane and carbon dioxide, and traces of other low boilers. At the bottom of the extractive distillation column, a bottom stream 17 comprising N-methylpyrrolidone, water, butanes, butenes and butadiene is withdrawn. The extractive distillation column used is a column containing 4.5 m of A3-1000 structured packing from Montz, divided into 8 packing sections. Above the structured packing are 14 bubble-cap trays. The bottom stream 9 withdrawn from the absorption column is added above the second packing section. 20 kg/h of the solvent comprising N-methylpyrrolidone and 8.3% by weight of water are added above the eighth packing section and below the bubble-cap trays. The inlet temperature of stream 13 is 35° C. The extractive distillation column is operated with a bottom temperature of 139° C., a top temperature of 46° C. and a pressure of 5 bara. The mass ratio of solvent 5 added to the absorption column to the solvent 13 added to the extractive distillation column is 0.8.

The bottom stream from the extractive distillation column is added as feed to a distillation column 19. In the distillation column, a top stream 21 comprising n-butane, butenes and butadiene, and a bottom stream 23 comprising N-methylpyrrolidone and water, are obtained. The distillation column used is a bubble-cap tray column having 48 bubble-cap trays. Above the last bubble-cap tray is installed the column condenser. The bottom stream 17 withdrawn from the extractive distillation column is added above the thirty-second bubble-cap tray. The stream 21 is withdrawn as a gaseous olefin-rich top product. The bottom stream 23 is cooled down to a temperature of 35° C. in the heat exchanger 27 and recycled into columns 3 and 11 (streams 5 and 13). The distillation column 19 is operated with a bottom temperature of 163° C., a temperature below the condenser of 31° C. and a pressure of 3 bara.

The top product stream 15 of the extractive distillation column is supplied to a condenser 20, and in the condenser a stream 18 comprising essentially carbon dioxide, hydrogen and n-butane, and a stream 16 comprising essentially n-butane are withdrawn. The stream comprising essentially n-butane is preferably recycled into a dehydrogenation for preparation of butenes and butadiene.

The composition and the amounts of the individual streams supplied or obtained in each case are listed in table 1.

Table 1: Composition of the Streams of a Workup of a Butene-Comprising Stream from an n-Butane Dehydrogenation in Mol %

TABLE 1

Composition of the streams of a workup of a butene-comprising stream from an n-butane dehydrogenation in mol %

| Stream | 1 | 7 | 15 | 21 | 16 | 18 |
|---|---|---|---|---|---|---|
| Hydrogen | 32.63 | 88.43 | 0.89 | 0.00 | 0.00 | 12.66 |
| Carbon monoxide | 0.20 | 0.61 | 0.00 | 0.00 | 0.00 | 0.00 |
| Ethane | 0.48 | 0.95 | 0.31 | 0.00 | 0.25 | 1.34 |
| Ethene | 0.03 | 0.04 | 0.03 | 0.00 | 0.01 | 0.13 |
| Propane | 0.94 | 1.06 | 1.62 | 0.00 | 1.69 | 2.14 |
| Propene | 0.36 | 0.06 | 0.97 | 0.00 | 0.94 | 1.47 |
| Carbon dioxide | 3.50 | 3.86 | 5.71 | 0.00 | 1.74 | 43.17 |
| Methane | 1.55 | 3.90 | 0.24 | 0.00 | 0.02 | 3.00 |
| i-Butane | 0.13 | 0.03 | 0.32 | 0.00 | 0.33 | 0.17 |
| n-Butane | 36.24 | 0.71 | 84.36 | 21.89 | 89.30 | 33.45 |
| trans-Butene-2 | 8.84 | 0.11 | 0.55 | 27.27 | 0.54 | 0.23 |
| 1-Butene | 7.18 | 0.03 | 4.20 | 23.59 | 4.41 | 1.93 |
| Isobutene | 0.10 | 0.00 | 0.04 | 0.27 | 0.04 | 0.02 |
| cis-Butene-2 | 6.73 | 0.18 | 0.69 | 23.15 | 0.65 | 0.26 |
| Butadiene | 1.09 | 0.02 | 0.06 | 3.82 | 0.06 | 0.03 |
| Amount, mol/h | 42.46 | 16.27 | 13.98 | 12.21 | 12.89 | 1.09 |

Example 2

A stream 1 comprising hydrogen, nitrogen, oxygen, n-butane, butenes and butadiene is added to an absorption column 3 in the lower region. In the upper region of the absorption column, the solvent introduced is N-methylpyrrolidone containing 8.3% by weight of water. At the top of the column, a top stream 7 comprising nitrogen, oxygen, hydrogen and butane is withdrawn. At the bottom, a bottom stream 9 comprising N-methylpyrrolidone, water, butanes, butenes, butadiene and carbon dioxide is obtained. The absorption column used is a column having 20 theoretical plates. The inlet temperature of the solvent, which is added at a molar flow rate of 9042 kmol/h, is 40° C. The absorption is performed at a top temperature of 41° C., a bottom temperature of 63° C. and a pressure of 10 bara. The molar flow ratio of solvent to added stream 1 comprising hydrogen, nitrogen, n-butane, butenes and butadiene is 2.7.

The bottom stream 9 withdrawn from the absorption column is added to an extractive distillation column 11 as a feed in the middle region. In the upper region, 901 kmol/h of a solvent comprising N-methylpyrrolidone and 8.3% by weight of water are added to the extractive distillation column. At the top of the extractive distillation column, a top product stream 15 is obtained, which comprises butane and carbon dioxide, and traces of other low boilers. The return stream at the top of the column is 99.5 kmol/h. At the bottom of the extractive distillation column, a bottom stream 17 comprising N-methylpyrrolidone, water, butanes, butenes and butadiene is withdrawn. The extractive distillation column comprises 48 theoretical plates. The stream 9 is supplied at the twenty-ninth theoretical plate, and stream 13 at the forty-sixth theoretical plate. The inlet temperature of stream 13 is 35° C. The extractive distillation column is operated with a bottom temperature of 103° C., a top temperature of 44° C. and a pressure of 4.8 bara. The mass ratio of solvent 5 added to the absorption column to the solvent 13 added to the extractive distillation column is 10.

The bottom stream from the extractive distillation column is added as feed to a distillation column 19. In the distillation column, a top stream 21 comprising n-butane, butenes and butadiene, and a bottom stream 23 comprising N-methylpyrrolidone and water, are obtained. The distillation column comprises 13 theoretical plates. The bottom stream 17 withdrawn from the extractive distillation column is added at the eleventh theoretical plate. The stream 21 is withdrawn as a gaseous olefin-rich top product. The return stream at the top of the column is 919 kmol/h. The bottom stream 23 is cooled in a heat exchanger 27 and recycled to columns 3 and 11 (streams 5 and 13). The distillation column 19 is operated at a bottom temperature of 171° C., a top temperature of 43° C. and a pressure of 4.7 bara.

The top product stream 15 of the extractive distillation column is supplied to a condenser 20, and a stream 18 comprising essentially carbon dioxide, hydrogen and n-butane, and a stream 16 comprising essentially n-butane, are withdrawn in the condenser. The stream comprising essentially n-butane is preferably recycled into a dehydrogenation for preparation of butenes and butadiene.

The composition and the amounts of the individual streams supplied or obtained in each case are listed in table 2.

TABLE 2

Composition of the streams of a workup of a stream comprising butadiene in mol %

| Stream | 1 | 7 | 15 | 21 | 16 | 18 |
|---|---|---|---|---|---|---|
| Butane | 4.56 | 3.74 | 85.63 | 1.20 | 87.44 | 23.66 |
| 1-Butene | 0.02 | 0.01 | 0.63 | 0.00 | 0.64 | 0.22 |
| C-2-Butene | 0.21 | 0.06 | 0.07 | 1.76 | 0.07 | 0.02 |
| T-2-Butene | 0.33 | 0.15 | 0.75 | 2.07 | 0.77 | 0.21 |
| 1,3-Butadiene | 9.25 | 0.01 | 0.04 | 93.16 | 0.04 | 0.01 |
| $H_2O$ | 0.54 | 0.22 | 1.86 | 1.81 | 1.91 | 0.17 |
| N-Methylpyrrolidone | | 0.01 | 0.00 | 0.00 | 0.00 | |
| $CO_2$ | 1.27 | 1.19 | 11.03 | 0.00 | 9.13 | 75.71 |
| $O_2$ | 0.02 | 0.02 | | | | |
| $H_2$ | 0.04 | 0.05 | | | | |
| $N_2$ | 83.77 | 94.54 | | | | |
| Amount, kmol/h | 3380 | 3002 | 146 | 330 | 43 | 4 |

List of reference numerals

1 Stream comprising butene and/or butadiene, butane, and hydrogen, with or without carbon dioxide
3 Scrubbing column
5 Stream comprising N-methylpyrrolidone and water
7 Top stream comprising hydrogen
9 Bottom stream comprising butene and/or butadiene, and scrubbing liquid, with or without carbon dioxide
11 Extractive distillation column
13 Stream comprising N-methylpyrrolidone and water
15 Top stream comprising butane
16 Butane-rich stream
17 Bottom stream comprising butene and/or butadiene, N-methylpyrrolidone and water, with or without carbon dioxide
18 Carbon dioxide-rich stream
19 Distillation column
20 Condenser
21 Top stream comprising butene and/or butadiene and carbon dioxide
23 Bottom stream comprising N-methylpyrrolidone and water
25 Condenser
27 Heat exchanger

The invention claimed is:

1. A process for workup of a stream (1) comprising butene and/or butadiene, butane, hydrogen and/or nitrogen and carbon dioxide, comprising the following steps:

(a) absorption of the stream (1) with a mixture (5) comprising 80 to 97% by weight of N-methylpyrrolidone and 3 to 20% by weight of water to obtain a stream (9) comprising N-methylpyrrolidone, water, butene and/or butadiene, and butane, with or without carbon dioxide, and a stream (7) comprising hydrogen and/or nitrogen and butane, (b) extractive distillation of the stream (9) with a stream (13) comprising 80 to 97% by weight of N-methylpyrrolidone and 3 to 20% by weight of water to separate the stream (9) into a stream (17) comprising N-methylpyrrolidone, water, butene and/or butadiene, and a stream (15) comprising essentially butane, with or without carbon dioxide, (c) distillation of the stream (17) into a stream (23) comprising essentially N-methylpyrrolidone and water, and a stream (21) comprising butene and/or butadiene.

2. The process according to claim 1, wherein the stream (15) is condensed to remove carbon dioxide.

3. The process according to claim 1, wherein at least a portion of the stream (23) removed in step (c) is recycled into the absorption and/or into the extractive distillation.

4. The process according to claim 1, wherein the absorption in step (a) is performed at a bottom temperature in the range from 30 to 160° C., a top temperature in the range from 5 to 60° C. and a pressure in the range from 2 to 20 bar.

5. The process according to claim 1, wherein the absorption in step (a) is performed in a column (3) to which the stream (5) the stream (1) are added in countercurrent.

6. The process according to claim 1, wherein the extractive distillation in step (b) is performed in an extractive distillation column (11) to which the stream (9) and the stream (13) are added in countercurrent.

7. The process according to claim 1, wherein the stream (7) removed in the absorption in step (a) is at least partly recycled into a butane dehydrogenation from which the stream (1) originates.

8. The process according to claim 1, wherein the butane removed in the extractive distillation in step (b) is recycled into a butane dehydrogenation.

9. The process according to claim 1, wherein the ratio of mixture of water and N-methylpyrrolidone added in the absorption in step (a) to the mixture of water and N-methylpyrrolidone added in the extractive distillation in step (b) is in the range from 0.2 to 20.

* * * * *